US008195293B2

(12) United States Patent
Limousin et al.

(10) Patent No.: US 8,195,293 B2
(45) Date of Patent: Jun. 5, 2012

(54) DETECTING VENTRICULAR NOISE ARTIFACTS IN AN ACTIVE IMPLANTABLE MEDICAL DEVICE FOR PACING, RESYNCHRONIZATION AND/OR DEFIBRILLATION OF THE HEART

(75) Inventors: Marcel Limousin, Paris (FR); Elodie Vincent, Antony (FR)

(73) Assignee: Sorin CRM S.A.S, Clamart (FR)

( * ) Notice: Subject to any disclaimer, the term of this patent is extended or adjusted under 35 U.S.C. 154(b) by 1113 days.

(21) Appl. No.: 11/750,494

(22) Filed: May 18, 2007

(65) Prior Publication Data

US 2007/0282379 A1 Dec. 6, 2007

(30) Foreign Application Priority Data

May 18, 2006 (FR) .................................... 06 04446

(51) Int. Cl.
*A61N 1/00* (2006.01)

(52) U.S. Cl. ........................................................ 607/14

(58) Field of Classification Search .......... 600/508–528; 607/5, 17, 18, 28
See application file for complete search history.

(56) References Cited

U.S. PATENT DOCUMENTS 5,304,208 A 4/1994 Inguaggiato et al.
5,462,060 A 10/1995 Jacobson et al.
5,496,351 A 3/1996 Plicchi et al.
5,647,379 A 7/1997 Meltzer
5,776,168 A 7/1998 Gunderson
5,868,793 A 2/1999 Nitzsche et al.
6,892,092 B2 5/2005 Palreddy et al.
7,092,759 B2 * 8/2006 Nehls et al. .................... 607/19
7,130,681 B2 * 10/2006 Gebhardt et al. ................ 607/6
7,366,566 B2 * 4/2008 Henry et al. ..................... 607/9
7,409,241 B2 * 8/2008 Vitali et al. ................... 600/513
2005/0209649 A1 * 9/2005 Ferek-petric .................. 607/17

FOREIGN PATENT DOCUMENTS

EP 0 515 319 11/1992
EP 0 626 182 11/1994
EP 0 653 225 5/1995
EP 0 655 260 5/1995
EP 0 838 235 4/1998
EP 1 433 496 6/2004
EP 1 533 001 5/2005
EP 1 537 894 6/2005
WO WO 2005/018738 3/2005

* cited by examiner

*Primary Examiner* — Eric D. Bertram
*Assistant Examiner* — Elizabeth K So
(74) *Attorney, Agent, or Firm* — Orrick Herrington & Sutcliffe, LLP

(57) ABSTRACT

Sensing ventricular noise artifacts in an active implantable medical device for pacing, resynchronization and/or defibrillation of the heart. This device concerns sensing heart rhythm through an endocardial electrode collecting the depolarization potentials, and detecting the myocardium contractions through an endocardial acceleration sensor. The device searches for ventricular noise artifacts (X, Y) by correlating the signals representative of successive ventricular and atrial depolarizations (P, R) with the signals representative of successive acceleration peaks (PEA I). In case of a lack of correlation, a signal of suspicion of ventricular noise is delivered, which temporarily modifies the sensing sensitivity (S) of the sensing circuit.

20 Claims, 2 Drawing Sheets

10 CONTINUOUS DETECTION OF PEA AND V
12 PEA: STABLE IN AMPLITUDE AND/ OR COUPLING INTERVALS ? — YES / NO
14 PEA: $F_{PEA} < F_{TACHYCARDIES}$ ? — YES / NO
16 V: SERIES OF V HAVE A SHORT AND VARIABLE COUPLING INTERVAL ? — YES / NO
18 SUSPICION OF V NOISE REDUCE THE V DETECTION SENSITIVITY
20 SUSPICION OF ARRYTHMIA ? — YES / NO
22 RESTORATION OF SENSITIVITY

DETECTING VENTRICULAR NOISE ARTIFACTS IN AN ACTIVE IMPLANTABLE MEDICAL DEVICE FOR PACING, RESYNCHRONIZATION AND/OR DEFIBRILLATION OF THE HEART

FIELD OF THE INVENTION

The present invention relates to "active implantable medical devices" as such devices are defined by the Jun. 20, 1990 Directive 90/385/GEE of the Counsel of the European Community, and more particularly to implantable devices that continuously monitor a patient's heart rhythm, and deliver to the heart, if need be, electrical pulses for pacing, resynchronization, cardioversion and/or defibrillation, in the case of a detection by the device of a heart rhythm disorder.

BACKGROUND OF THE INVENTION

Analysis of the heart rhythm is made based upon electrogram (EGM) signals, collected using electrodes mounted on endocardial leads, implanted in the myocardium. From the EGM, one can measure the atrial and/or ventricular depolarization potential. These signals are then analyzed by the implantable device (IMD), which, when appropriate, will deliver to the patient an appropriate therapy. The therapy delivered may be, for example, in the form of low energy pulses (anti-bradycardia pacing or ventricles resynchronization pacing) or cardioversion or defibrillation shocks.

However, the rhythm analysis, and therefore the decision to deliver or not a therapy, may be altered by artifacts collected by the endocardial lead.

These artifacts can have various origins. A first series of artifacts corresponds to such situations when the device not only detects the event as such, i.e, the depolarization wave of the considered cavity, but also a disturbance that is associated with that same event and considered, erroneously, as another event occurring after said first event: e.g., a late depolarization wave, cross-talk between the two cavities, etc.

Another series of artifacts are those to which the present invention is directed, namely artifacts of extrinsic noise not related to the myocardium depolarization. This noise can have various origins: notably, the myopotentials associated with muscular contractions, as well as electromagnetic interference (EMI) coming from different electronic equipment, such as surveillance devices, current daily-life devices, electro-surgical devices, communication systems, etc.

Such noise, if present with more or less regularity, can then be detected by the IMD as a myocardium depolarization, with a risk to generate inappropriate therapies, for instance by erroneously inhibiting the antibradycardia pacing therapy or resynchronization therapy, or, conversely, by erroneously delivering inappropriate shocks.

Various techniques have been proposed to reduce the influence of such extrinsic noises, notably the application of analog or digital filtering, the implementation of refractory periods, the automatic adaptation of sensing amplifier sensitivity, or the automatic gain control of these amplifiers.

However, the use of such techniques is always detrimental towards a good sensing.

In particular, in order to ensure the sensing of ventricular fibrillation (VF) with a low signal level, it is necessary to seek a maximal sensing sensitivity, so as to minimize the risk not to sense some events that should have been sensed. Indeed, the amplitude of VF signals may have a variable level comprised between the level of noise signals likely to be sensed by the IMD, and that of the signals of sinus complexes. If ventricular fibrillation has to be sensed, the sensing of a potential noise therefore cannot be avoided. If, moreover, a steady noise is present, with a patient presenting a normal cardiac sinus rhythm, such noise may be confused with depolarizations. That situation may distort the evaluation of the average rhythm by the IMD, such rhythm being evaluated at a level much higher than reality, with a correlative risk for applying an undesirable antitachycardia therapy (false positive). Conversely, if the IMD is set with too low a sensitivity, that is with a sensing threshold too high, the true episodes of ventricular fibrillation may not be sensed (false negative), with consequences that are much more severe towards the patient.

OBJECTS AND SUMMARY OF THE INVENTION

As sensing of extrinsic noise is commonly unavoidable, the present invention is directed to overcoming the problem of discriminating such noise from cardiac depolarizations, in order to prevent triggering of inappropriate therapies caused by this noise of external origin.

The starting point of the present invention lies in the observation that the depolarization, which is an electrical phenomenon that is sensitive to noise, is usually followed by a cardiac contraction, which is a mechanical phenomenon that is not affected by noise. Hence, by proceeding to a double sensing—of both depolarization and contraction—by separate devices, it is possible, in the presence of suspect noise, to obviate the doubt and confirm that the sensed signal has been actually followed by a mechanical activity of the heart, and therefore properly represents a depolarization signal, and not an artifact.

Sensing the mechanical activity of the heart is known and can preferably be operated through the measurement of endocardial acceleration, by means of an accelerometer placed directly in contact with the heart muscle (usually level with the right ventricular apex). Indeed, it is known that endocardial acceleration reflects very precisely, and in real-time, the phenomena concurring to the mechanical operation of the heart.

More particularly, the issued European patent EP 0,515,319, and its U.S. counterpart U.S. Pat. No. 5,304,208 (assigned to Sorin Biomedica S.p.A.) teach structure and techniques to collect an endocardial acceleration signal by using an endocardial lead equipped with a distal pacing electrode implanted into the ventricle and integrating a micro-accelerometer allowing to measure the endocardial acceleration.

The endocardial acceleration signal thus collected during a cardiac cycle notably presents two peaks corresponding to the two major noises that can be identified along each cycle of a normal heart:

- the first endocardial acceleration peak ("PEA I") corresponds to the closure of mitral and tricuspid valves, at the beginning of the phase of isovolumetric ventricular contraction (systole). The variations of this first peak are closely related to pressure variations in the ventricle (the amplitude of PEA I peak, being more precisely correlated to the positive maximum of pressure variation, dP/dt, in the left ventricle) and can therefore constitute a representative parameter for myocardium contractility.
- The second peak of endocardial acceleration ("PEA II") corresponds to the closure of aortic and pulmonary valves, at the beginning of the diastole. It is produced by the brutal deceleration of moving blood mass in the aorta.

The issued European patent EP 0,655,260 and its U.S. counterpart U.S. Pat. No. 5,496,351 (assigned to Sorin Biomedica S.p.A.) describe processing the endocardial acceleration signal provided by the sensor located at the tip of the lead, so as to compute two respective values related to these peaks of endocardial acceleration.

These documents propose to use the amplitude values of the peaks PEA I and PEA II in order to detect the heart disorders, and trigger or not a defibrillation therapy.

In the case of the present invention, the principle is to detect the presence or absence of a heart contraction, based upon the principle that each true heart cycle corresponds to one single cardiac contraction. The endocardial acceleration is analyzed, advantageously by detecting the presence or absence of a PEA I peak, to confirm the presence of a mechanical activity of the heart upon detection of a depolarization: such a detection that would not be followed by a mechanical activity of the heart may have been generated by noise. It is therefore suspect and shall not systematically lead to application or inhibition (depending on the case) of a therapy.

Broadly, the device of the present invention is of the same type as that described in EP 0,655,260 and U.S. Pat. No. 5,496,351 cited above, i.e., a device comprising:

- means for sensing a patient's heart rhythm comprising at least one endocardial electrode able to collect the electrical potential related to the myocardium depolarizations, and a sensing circuit able to analyze the collected potentials and deliver a sequence of signals representative of the successive ventricular and atrial depolarizations, and
- means for sensing the myocardium contractions comprising an endocardial acceleration sensor, and means for determining at least one peak of endocardial acceleration over one given cardiac cycle and delivering a sequence of signals representative of successive acceleration peaks.

In a manner characteristic of the invention, the device also includes means for searching for ventricular noise artifacts, comprising means for receiving as input, and correlating together, said signals representative of the depolarizations and said signals representative of the peaks of endocardial acceleration and, in case of lack of correlation, de-liver a signal of suspicion of ventricular noise.

In a preferred embodiment, the device also can include means for modifying an operating parameter of said means for sensing the patient's heart rhythm, in response to the delivery of a signal of suspicion of ventricular noise.

The operating parameter can preferably be a sensing threshold of the sensing circuit, modified so as to be increased in response to the delivery of a signal of suspicion of ventricular noise. Alternately, the operating parameter can be the parameter of a digital filter of the sensing circuit, modified toward a more restrictive filtering in response to the delivery of a signal of suspicion of ventricular noise.

The operating parameter is preferably being modified for a predetermined duration, or during a predetermined number of cycles, following the delivery of the signal of suspicion of ventricular noise. Preferably, however, the operating parameter is restored to its previous value in case of a suspicion of arrhythmia. The suspicion of arrhythmia can preferably arise from analyzing the successive ventricular and atrial depolarizations, or from use of means for sensing of an acceleration of the peaks of cardiac contractions, e.g., PEAs.

The device can preferably comprise two distinct endocardial leads, one equipped with said endocardial electrode, the other with said endocardial acceleration sensor.

The delivery of a signal of suspicion of ventricular noise is notably conditioned by the detection:

- of a sequence of acceleration peaks with a stable amplitude and/or stable coupling intervals,
- of a sequence of acceleration peaks with a frequency that is lower than a limiting value representative of a threshold of detection of tachycardiae, and/or
- of a sequence of depolarizations presenting successive coupling intervals that are short and variable.

The acceleration sensor can be a sensor able to assess the acceleration level with a ventricle, an atrium, or a peripheral heart blood vessel.

BRIEF DESCRIPTION OF THE DRAWINGS

Further features, characteristics and advantages of the present invention will become apparent to a person of ordinary skill in the art from the following detailed description of a preferred embodiment of the present invention, made with reference to the drawings annexed hereto, in which.

DETAILED DESCRIPTION OF THE INVENTION

Figure 1:
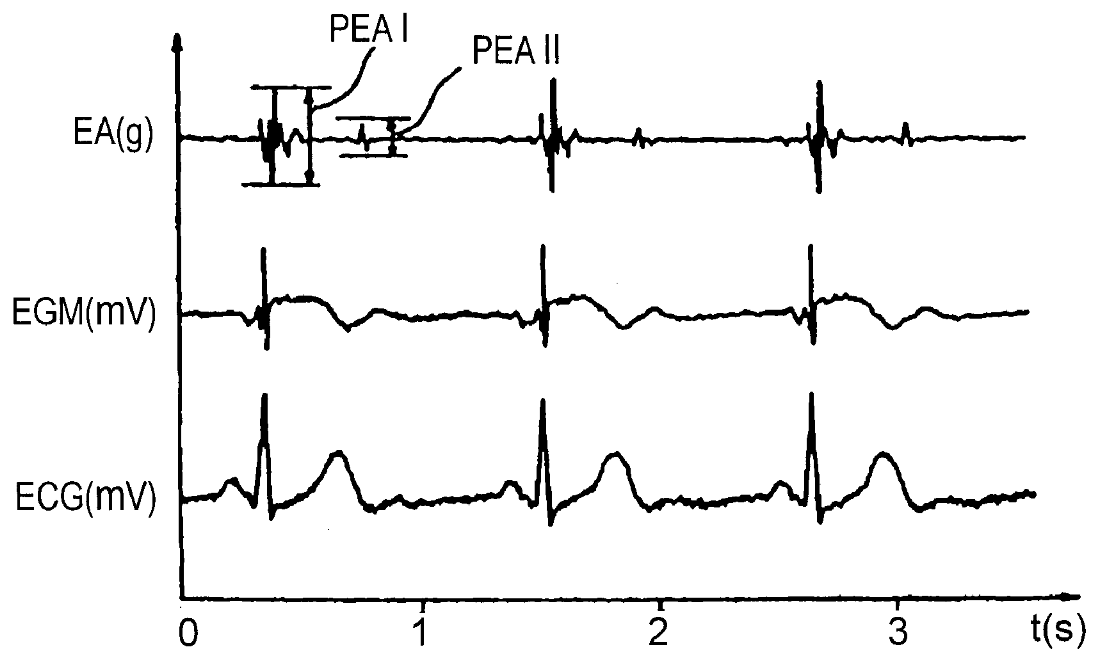
FIG. 1 is a time diagram showing, over three successive cardiac cycles, the variations of the endocardial acceleration as well as the electrogram and surface electrocardiogram.
Figure 2:
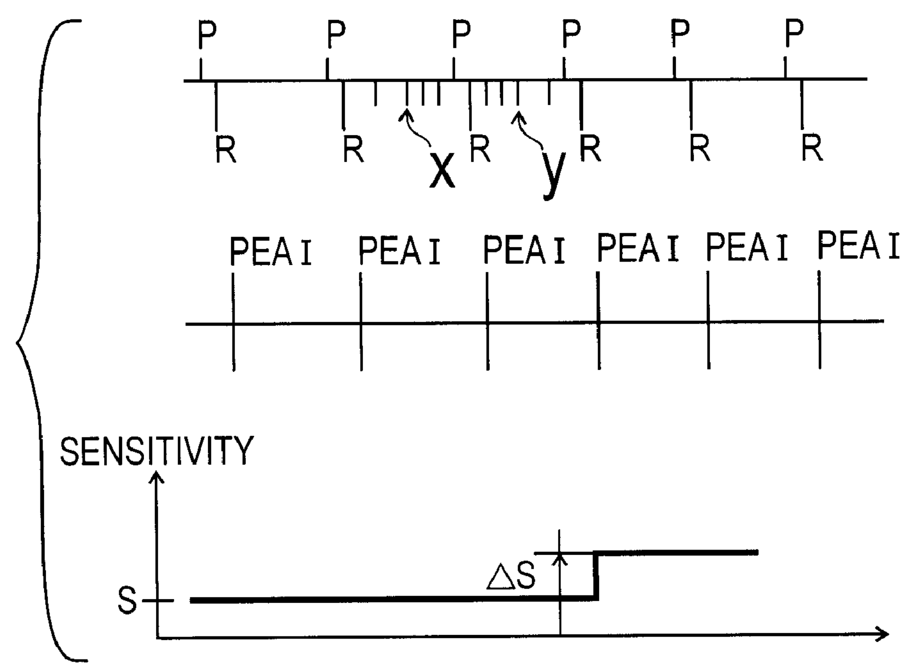
FIG. 2 is a time diagram, showing, over six successive cardiac cycles: (i) the different collected signals representative of successive depolarizations, (ii) the signal indicating the presence of an endocardial acceleration peak, and (iii) the changes brought to the sensing sensitivity in the presence of noise.
Figure 3:
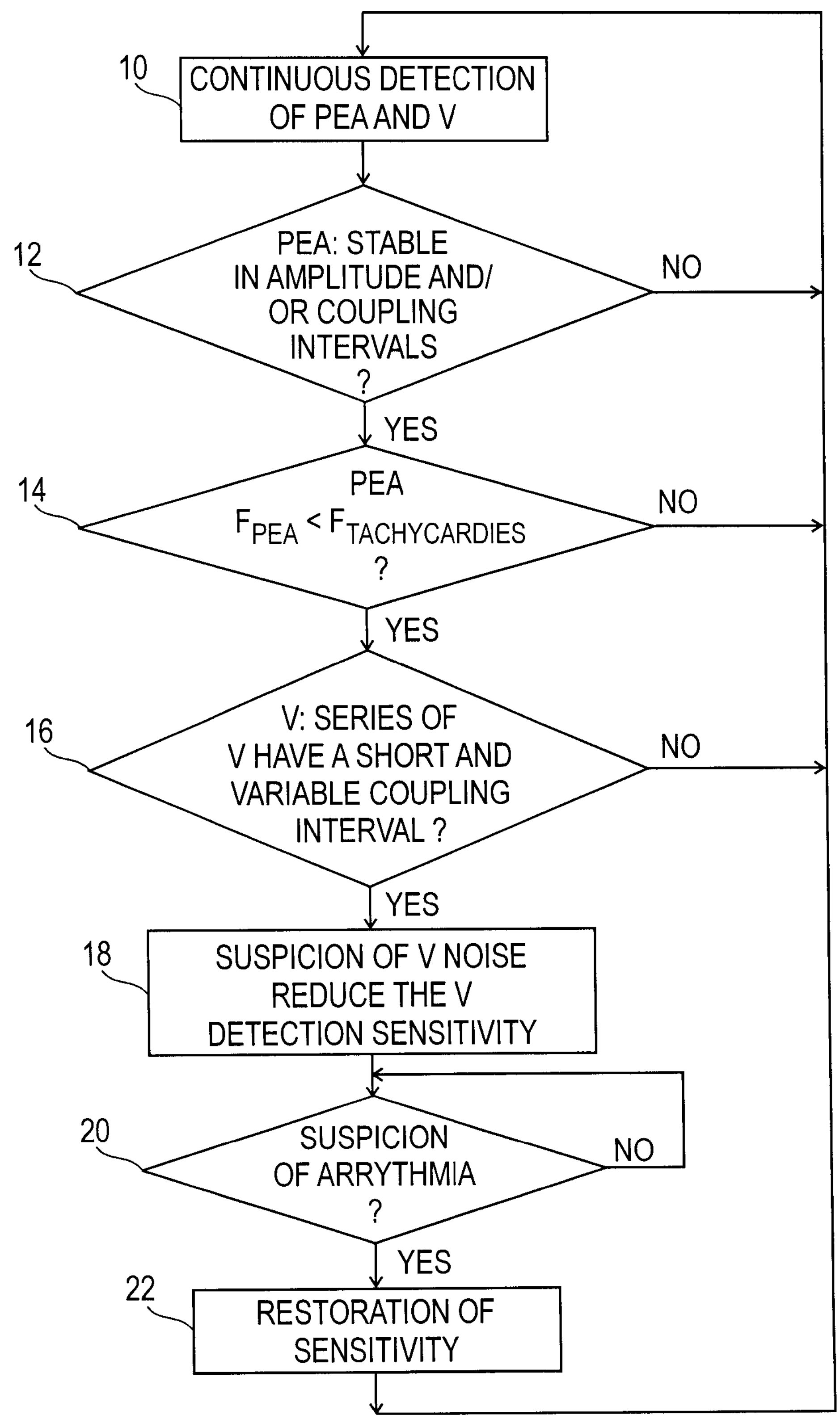
FIG. 3 is a flowchart showing the successive different steps of analysis for the implementation of the invention.

One will now describe a preferred embodiment of the device of this invention, with reference to FIGS. 1-3.

Regarding the software-related aspects thereof, the present invention can be implemented by an appropriate programming of the soft-ware of a known active implantable device, for example, of the pacemaker or defibrillator/cardiovertor type, comprising means for acquiring a signal provided by endocardial leads and/or one or more implanted sensors.

The invention can notably be applied to the implantable devices ELA Symphony and Rhapsody pacemakers marketed by ELA Medical, Montrouge, France.

These devices are equipped with programmable microprocessors, including circuits intended to acquire, format and process electrical signals collected by implanted electrodes, and deliver pacing pulses to these electrodes. It is also possible to upload towards these devices, by telemetry, software routines (updates, enhancements and new programs), that will be stored in internal memory and run so as to implement, among other things, the features of the invention, described in more detail below. Implementing the features of the invention into these devices is deemed to be within the abilities of a person of ordinary skill in the art, and will therefore not be described in detail in this document.

On FIG. 1, the upper curve shows the variations of endocardial acceleration (EA), measured through a sensor of the type described in EP 0,515,319 and U.S. Pat. No. 5,304,208 cited above, embedded in the tip of an endocardial lead placed in the apex of the ventricle.

FIG. 1 also shows the electrogram (EGM) traces, i.e., of the electrical signal collected through the distal electrode of the same lead, and a corresponding surface electrocardiogram (ECG), over three successive cardiac cycles. As explained above, the trace of acceleration presents two successive complexes or peaks of endocardial acceleration (PEA), parameters of which (amplitude, width and time position, that is:

moment of occurrence) can be determined by an appropriate processing of the signal provided by the acceleration sensor, as described in EP 0,655,260 and U.S. Pat. No. 5,496,351 cited above.

The present invention proposes to use the parameters correlated to the endocardial acceleration thus collected, preferably the occurrence of PEA I peak (indicated by the time position of this peak), in order to confirm or not the presence of a mechanical activity of the heart.

The first line of FIG. 2 shows the succession of atrial (P) and ventricular (R) events, over six successive cardiac cycles, for a patient presenting a normal sinus rhythm.

Collection of these signals may be disturbed by the sensing of extrinsic ventricular noises that can be seen as artifacts, such as those illustrated in X and Y, likely to be (wrongly) interpreted by the IMD as ventricular events leading to an erroneous suspicion of a brutal increase of the ventricular rate, similar to what could happen in case of ventricular fibrillation.

However, the sequence of acceleration peaks (the second line in FIG. 2) is not affected by noise, for it reflects the sensing of a purely mechanical activity, as explained above.

The steady character of the contractions allows one to obviate the suspicion of ventricular fibrillation and to qualify the suspect events X and Y as artifacts.

In order to prevent from sensing this ventricular noise during the following cardiac cycles, it is advantageous to modulate the sensitivity of the depolarization sensing circuits, by increasing the sensing threshold S by an increment ΔS (the third line in FIG. 2), for a predetermined duration, or during a predetermined number of cycles. This reduction of sensitivity (increment ΔS) can eventually be modulated as a function of sensed noise.

One will now describe, with reference to the flowchart on FIG. 3, a preferred correlation between the signals representative of the depolarizations (the first line in FIG. 2) and those representative of the acceleration peaks (the second line in FIG. 2).

The first step (10) consists of collecting in a continuous way, the endocardial acceleration signals and the ventricular depolarizations (V), the analysis being performed for each cardiac cycle.

The device determines, based upon those measurements, a first series of signals representative of the ventricular depolarizations, and a second series of signals representative of the acceleration peaks (PEA) (preferably the PEA I peak).

The first phase of the analysis (step 12) determines whether the PEA signals are stable in amplitude and/or in coupling intervals (the coupling interval being the time period between two peaks relating to successive cycles). The condition of stability in amplitude means, for example, that the PEA I peak amplitude does not vary by more than x % compared to the average of the previous y cycles. The condition of stability of coupling intervals means, for example, that the coupling interval does not vary by more or less z milliseconds, for instance plus or minus 30 milliseconds from one cycle to the next.

In the presence of a stable PEA rhythm, revealing regular con-tractions, the device determines (step 14) whether the rate of these con-tractions (frequency of PEA peaks ($f_{PEA}$)) is lower than a limiting rate, lower than the detection zone of tachycardiae ($f_{tachycardiae}$).

If not, then the heart rhythm is probably a confirmed tachycardia, for which a therapy shall be considered, with no need to perform the analysis any further.

Otherwise, that is, in the presence of a rhythm of contractions that is sufficiently low, the device examines (step 16) whether it is in presence of a series of ventricular events with a short and variable coupling interval (the criterion of "short coupling" means that the coupling intervals between successive ventricular events are lower than a given threshold, and the criterion of "variable coupling" means that the differences between the coupling intervals are higher than a given threshold over a predetermined number of successive cycles).

If the analysis of the ventricular depolarizations reveals (at step 16) a fast and unstable rhythm, then ventricular noise is suspected (step 18).

In order to prevent from sensing such ventricular noise over the following cycles, the sensitivity of the ventricular sensing circuit is reduced (which means the sensitivity threshold is increased) for a predetermined period of time (time being defined in terms of duration or in terms of a number of cycles). It can be noted that in the alternative or optionally also some other operating parameters of the sensing circuits may be modified in case of suspected ventricular noise, notably the adjustment of the circuits or filtering algorithms.

It is anyhow necessary to restore, as fast as possible, the ventricular sensitivity to its initial setting, in case of suspected arrhythmia or of loss of sinus signal (steps 20, 22).

The detection of arrhythmiae can notably be implemented through the algorithm "PARAD" (registered trade mark of ELA Medical), which is a diagnostic algorithm, notably described in issued European patents EP 0,626,182 and EP 0,838,235 and their respective U.S. counterparts U.S. Pat. Nos. 5,462,060 and 5,868,793 (commonly assigned herewith to ELA Medical), to which one seeking for further details may refer.

That detection can also be implemented through the detection of an acceleration of the cardiac contraction peaks: for example, an acceleration of 25% of the average of the previous 8 intervals will be considered as a situation corresponding to a suspicion of arrhythmia.

In an alternate embodiment, the detection of noise can be used to modify the sensing algorithms associated with ventricular therapies so as to prevent delivery of inappropriate therapies. For example, the treatment of an arrhythmia that presents more than a given percentage (e.g. 50%) of "noisy" cycles, may be delayed by a preselected time period, which time period can be greater or lesser depending on a corresponding greater or lesser amount of detected noise, i.e., a time period whose duration varies as function of the percentage of noisy cycles detected in a given interval or number of cycles.

Although the description above is made with reference to a device collecting the signals of endocardial acceleration at the level of the right ventricle, this characteristic is in no way limitative, and the invention can equally be implemented by using signals that are representative of the endocardial acceleration measured level with:

an atrium, the left ventricle, a blood vessel that is peripheral to the heart, that is a vessel located on the heart, or at immediate proximity thereof (in contact with the heart wall).

One skilled in the art will appreciate that the present invention can be practiced by other than the embodiments described herein, which embodiments are presented for purposes of illustration and not of limitation.

We claim:

1. An active implantable medical device for pacing, resynchronization, cardioversion and/or defibrillation of the heart, comprising:

a means for sensing a patient's heart rhythm, comprising a sensing circuit, the sensing circuit collecting signals that are representative of cardiac depolarizations from at least one endocardial electrode adapted to be implanted in the myocardium of the patient;

means for detecting myocardium contractions of the patient's heart, comprising an endocardial acceleration sensor and means for determining at least one endocardial acceleration peak over one given cardiac cycle, wherein the endocardial acceleration sensor senses signals that are representative of endocardial acceleration peaks (PEA);

means for searching for ventricular noise artifacts, comprising means for performing correlation analysis between said signals representative of the cardiac depolarizations and said signals representative of the endocardial acceleration peaks, and means for delivering, in the case of a lack of correlation, a signal of ventricular noise suspicion, means for detecting a level of noise signals in the signals representative of cardiac depolarizations, and a means for modifying an operating parameter of said means for sensing the patient's heart rhythm as a function of said level of noise signals.

2. The device of claim 1, wherein the operating parameter of said means for sensing the patient's heart rhythm is modified in response to the delivery of the signal of ventricular noise suspicion.

3. The device of claim 2, wherein said operating parameter is a sensitivity threshold (S) of said sensing circuit, and the means for modifying the operating parameter comprise means for increasing the sensitivity threshold by a predetermined amount (ΔS), in response to the delivery of the signal of ventricular noise suspicion.

4. The device of claim 2, wherein the sensing circuit further comprises a digital filter and said operating parameter is a parameter of said digital filter, and the means for modifying the operating parameter further comprises means for modifying the parameter of said digital filter towards a more restrictive filtering, in response to the delivery of the signal of ventricular noise suspicion.

5. The device of claim 2, wherein the means for modifying the operating parameter further comprises means for modifying said operating parameter for a predetermined duration, or during a predetermined number of cycles, following the delivery of the signal of ventricular noise suspicion.

6. The device of claim 1, wherein the sensing circuit provides signals that are representative of successive ventricular and atrial depolarizations, and the device further comprises means for analyzing said signals representative of the successive ventricular and atrial depolarizations, and wherein the means for modifying the operating parameter further comprises means for restoring the operating parameter to its previous setting in a case of suspicion of an arrhythmia.

7. The device of claim 6, wherein the means for restoring the operating parameter comprises means for analyzing the successive ventricular and atrial depolarizations.

8. The device of claim 7, wherein the means for restoring the operating parameter further comprises means for detecting an acceleration of the endocardial acceleration peaks.

9. The device of claim 1, further comprising two distinct endocardial leads, one equipped with said endocardial electrode, the other with said endocardial acceleration sensor.

10. The device of claim 1, wherein the delivery of the signal of ventricular noise suspicion is conditioned by the detection of a sequence of endocardial acceleration peaks with a rate that is lower than a limiting rate representative of a threshold of tachycardia detection.

11. The device of claim 1, wherein the delivery of the signal of ventricular noise suspicion is conditioned by the detection of a sequence of cardiac depolarizations presenting short and variable successive coupling intervals.

12. The device of claim 1, wherein the endocardial acceleration sensor is a sensor sensing an acceleration level of a heart ventricle.

13. The device of claim 1, wherein the endocardial acceleration sensor is a sensor sensing an acceleration level of a heart atrium.

14. The device of claim 1, wherein the endocardial acceleration sensor is a sensor sensing an acceleration level of a blood vessel that is peripheral to the patient's heart.

15. The device of claim 1 further comprising means for delivering a ventricular therapy in accordance with an algorithm responsive to the signals representative of cardiac depolarizations and endocardial acceleration peaks, and means for modifying said algorithm to delay delivery of said ventricular therapy in response to the delivery of the signal of ventricular noise suspicion.

16. The device of claim 15, wherein said delay of said ventricular therapy further comprises a time period having a duration that is a function of a percentage of noisy cycles detected.

17. An active implantable medical device for pacing, resynchronization, cardioversion and/or defibrillation of the heart, comprising:

means for sensing a patient's heart rhythm, comprising a sensing circuit, the sensing circuit collecting signals that are representative of cardiac depolarizations from at least one endocardial electrode adapted to be implanted in the myocardium of the patient;

means for detecting myocardium contractions of the patient's heart, comprising an endocardial acceleration sensor and means for determining at least one endocardial acceleration peak over one given cardiac cycle, wherein the endocardial acceleration sensor senses signals that are representative of endocardial acceleration peaks (PEA);

means for searching for ventricular noise artifacts comprising means for performing correlation analysis between said signals representative of the cardiac depolarizations and said signals representative of the endocardial acceleration peaks, and means for delivering, in the case of a lack of correlation, a signal of ventricular noise suspicion, wherein the delivery of the signal of ventricular noise suspicion is conditioned on the detection of a sequence of endocardial acceleration peaks that are stable in terms of amplitude and/or coupling intervals.

18. The device of claim 17, wherein operating parameter of said means for sensing the patient's heart rhythm is modified in response to the delivery of the signal of ventricular noise suspicion.

19. The device of claim 17, wherein the sensing circuit provides signals that are representative of successive ventricular and atrial depolarizations, and the device further comprises means for analyzing said signals representative of the successive ventricular and atrial depolarizations, and wherein the means for modifying the operating parameter further comprises means for restoring the operating parameter to its previous setting in a case of suspicion of an arrhythmia.

20. The device of claim 19, wherein the means for restoring the operating parameter comprises means for analyzing the successive ventricular and atrial depolarizations.

* * * * *